(12) United States Patent
Jensen et al.

(10) Patent No.: US 9,883,849 B2
(45) Date of Patent: Feb. 6, 2018

(54) ULTRASOUND IMAGING

(75) Inventors: Henrik Jensen, Bagsvaerd (DK); Gert Seerup, Hillerod (DK); Jan Peter Bagge, Stenlose (DK)

(73) Assignee: B-K Medical Aps, Herlev (DK)

( * ) Notice: Subject to any disclaimer, the term of this patent is extended or adjusted under 35 U.S.C. 154(b) by 287 days.

(21) Appl. No.: 14/410,834

(22) PCT Filed: Jun. 28, 2012

(86) PCT No.: PCT/IB2012/001295
§ 371 (c)(1),
(2), (4) Date: Dec. 23, 2014

(87) PCT Pub. No.: WO2014/001833
PCT Pub. Date: Jan. 3, 2014

(65) Prior Publication Data
US 2015/0126870 A1    May 7, 2015

(51) Int. Cl.
*G01S 15/89* (2006.01)
*A61B 8/00* (2006.01)
(Continued)

(52) U.S. Cl.
CPC ............ *A61B 8/4488* (2013.01); *A61B 8/085* (2013.01); *A61B 8/5207* (2013.01); *G01S 7/521* (2013.01);
(Continued)

(58) Field of Classification Search
CPC ...... G01S 15/89; G01S 7/521; G01S 15/8927; G01S 7/52038; G01S 15/8997;
(Continued)

(56) References Cited

U.S. PATENT DOCUMENTS 5,825,117 A    10/1998 Ossmann et al.
6,027,448 A    2/2000 Hossack et al.
(Continued)

OTHER PUBLICATIONS

Kazimierz T. Szopinski, MD et al., Tissue Harmonic Imaging Utility in Breat Sonography, 2003 by the American Institute of Ultrasound in Medicine; J Ultrasound Med 22:479-487, 2003.
(Continued)

*Primary Examiner* — Sanjay Cattungal
(74) *Attorney, Agent, or Firm* — Anthony M. Del Zoppo, III; Driggs, Hogg, Daugherty & Del Zoppo, Co., LPA (57) ABSTRACT

A method includes concurrently exciting neighboring pairs of transducer elements of an array for at least two transmits, wherein the array has a focus in a range of ten to twenty centimeters with a f-number of five or less. The method further includes receiving first echoes with individual transducer elements of a first sub-set of the transducer elements for a first of the at least two transmits, and receiving second echoes with individual transducer elements of a second sub-set of the transducer elements for a second of the at least two transmits. The method further includes extracting second harmonics from the echoes of the at least two transmits. The method further includes beamforming the extracted second harmonics. The method further includes generating an image based on the beamformed extracted second harmonics.

19 Claims, 5 Drawing Sheets

(51) Int. Cl.
*A61B 8/08* (2006.01)
*G01S 7/52* (2006.01)
*G01S 7/521* (2006.01)

(52) U.S. Cl.
CPC .......... *G01S 7/52038* (2013.01); *G01S 15/89* (2013.01); *G01S 15/8927* (2013.01); *G01S 15/8963* (2013.01); *G01S 15/8997* (2013.01); *A61B 8/4494* (2013.01); *A61B 8/486* (2013.01)

(58) Field of Classification Search
CPC . G01S 15/8963; A61B 8/4488; A61B 8/5207; A61B 8/085; A61B 8/486; A61B 8/4494
USPC .................................................. 600/437–469
See application file for complete search history.

(56) References Cited

U.S. PATENT DOCUMENTS

| | | | |
|---|---|---|---|
| 6,104,670 A | | 8/2000 | Hossack et al. |
| 6,206,833 B1 | | 3/2001 | Christopher |
| 6,425,869 B1 | | 7/2002 | Rafter et al. |
| 6,532,819 B1 | | 3/2003 | Chen et al. |
| 6,540,683 B1 | | 4/2003 | Lin |
| 6,645,146 B1 | | 11/2003 | Adams et al. |
| 6,656,123 B2 | | 12/2003 | Jensen et al. |
| 7,056,290 B2 | | 6/2006 | Rielly et al. |
| 7,635,332 B2 | | 12/2009 | Ladabaum et al. |
| 2001/0020131 A1 | | 9/2001 | Kawagishi et al. |
| 2004/0044284 A1 | | 3/2004 | Von Behren et al. |
| 2005/0054925 A1* | 3/2005 | Hao .................. | G01S 7/52038 600/443 |
| 2006/0173339 A1* | 8/2006 | Tornes ................ | A61K 9/0009 600/458 |
| 2006/0173342 A1 | 8/2006 | Panda et al. | |
| 2007/0038082 A1* | 2/2007 | Mo ......................... | B06B 1/064 600/437 |
| 2008/0214934 A1* | 9/2008 | Lee ...................... | A61B 8/5276 600/437 |
| 2009/0187106 A1* | 7/2009 | Lee ....................... | A61B 8/481 600/458 |
| 2010/0168575 A1* | 7/2010 | Hashiba .............. | G01S 7/52038 600/443 |
| 2012/0179044 A1* | 7/2012 | Chiang ..................... | A61B 8/14 600/447 |
| 2014/0254307 A1* | 9/2014 | Zhao ....................... | G01S 7/523 367/7 |
| 2015/0126870 A1* | 5/2015 | Jensen ................... | A61B 8/085 600/447 |

OTHER PUBLICATIONS

Sabina Ghoudhry, MD, et al., Comparison of Tissue Harmonic Imaging with Conventional US in Abdominal Disease, Imaging & Therapeutic Technology, RG vol. 20, No. 4, Jul.-Aug. 2000; pp. 1127-1135.
Boedeker Plastics, Inc., TPX Polymethylpententene Specifications, 904 West 6th Street, Shiner, TX 77984 USA.
Philip W. Ralls MD, Tissue Harmonic Imaging in Ultrasound Scanner Explained, Nova Imaging, DigiVision Digital Radiography. Ultrasound Technology Update; Harmonic Imaging, p. 1-6, GE Medical Systems, PO Box 414, Milwaukee, WI 53201 USA.
International Search Report for PCT/IB2012/001295, published as WO2014/001833, dated Mar. 19, 2013.

\* cited by examiner

ULTRASOUND IMAGING

RELATED APPLICATION

This application is a national filing of PCT application Serial No. PCT/IB2012/001295, filed Jun. 28, 2012, published as WO/2014/001833 on Jan. 3, 2014.

TECHNICAL FIELD

The following generally relates to ultrasound imaging and more particularly to harmonic ultrasound imaging with a phase array transducer for deep (e.g., ten centimeters or greater) scanning.

BACKGROUND

Ultrasound imaging provides useful information about the interior characteristics of an object or subject under examination. Conventional B-mode ultrasound imaging is performed by actuating a set of transducer elements to form an ultrasound beam having a fixed transmit focal point and sweeping the ultrasound beam through an examination area while transmitting pulses and detecting echoes. The echoes are delayed and summed to form B-mode scan lines, which are processed to generate images, which can be displayed via a monitor.

Harmonic imaging is similar to B-mode imaging except that one or more harmonic components (instead of the fundamental component) of the echoes are processed to generate the image. With harmonic imaging, the second harmonic component, for example, will have a frequency that is two times the frequency of the fundamental component, which results in a higher resolution image, relative to B-mode imaging. Unfortunately, harmonic imaging approaches have not been well-suited for deep penetration harmonic imaging (e.g., ten centimeters or greater) with the harmonics tending to dampen out between five to ten centimeters.

As such, harmonic imaging generally is not used for deep scanning. A solution has been to use harmonic imaging for shorter depths and then switch to from harmonic imaging to B-mode imaging at longer depths, even though the transducer is being operated in harmonic imaging mode. However, when imaging objects such as kidney stones, which generally are located at longer depths, artifact such as ghosting or mirroring may be introduced into the images. In view of the above, there is an unresolved need for other approaches to harmonic imaging.

SUMMARY

Aspects of the application address the above matters, and others.

In one aspect, an ultrasound imaging system includes a transducer, including: an array of a plurality of transducer elements that emit ultrasonic signals that traverse an object in an imaging field of view and receive echoes generated in response to an interaction between the ultrasonic signals and the object, wherein the transducer has a focus in a range of ten to twenty centimeters with a f-number of five or less. The ultrasound imaging system further includes transmit circuitry that generates a first set of first excitation pulses that excites the plurality of transducer elements to emit first ultrasonic signals and, after a predetermined time delay, a second set of second excitation pulses that excites the of plurality of transducer elements to emit second ultrasonic signals, wherein the transmit circuitry sequentially excites groups of two or more transducer elements with the first set of first excitation pulses and with the second set of second excitation pulses, exciting all of the transducer elements in each excitation. The ultrasound imaging system further includes receive circuitry that receives first echoes generated in response to the first set of first excitation pulses and received by a first sub-set of the transducer elements and extracts a first set of harmonic components from the first echoes, and that receives second echoes generated in response to the second set of second excitation pulses and received by a second different sub-set of the transducer elements and extracts a second set of harmonic components from the second echoes. The ultrasound imaging system further includes a beamformer that beamforms the extracted first set of harmonic components producing first intermediate data and beamforms the extracted second set of harmonic components producing second intermediate data.

In another aspect, a method includes transmitting a first set of first excitation pulses that excites a plurality of transducer elements of a phase array to emit first ultrasonic signals and, after a predetermined time delay, a second set of second excitation pulses that excites the of plurality of transducer elements to emit second ultrasonic signals, wherein groups of two or more transducer elements are sequentially excited with the first set of first excitation pulses and with the second set of second excitation pulses. The method further includes receiving first echoes generated in response to the first set of first excitation pulses and received by a first sub-set of the transducer elements and extracting a first set of harmonic components from the first echoes, and receiving second echoes generated in response to the second set of second excitation pulses and received by a second different sub-set of the transducer elements and extracting a second set of harmonic components from the second echoes. The method further includes beamforming the extracted first set of harmonic components producing first intermediate data and beamforming the extracted second set of harmonic components producing second intermediate data. The transducer has a focus in a range of ten to twenty centimeters and a f-number of five or less.

In another aspect, a method includes concurrently exciting neighboring pairs of transducer elements of an array for at least two transmits, wherein the array has a focus in a range of ten to twenty centimeters with a f-number of five or less. The method further includes receiving first echoes with individual transducer elements of a first sub-set of the transducer elements for a first of the at least two transmits, and receiving second echoes with individual transducer elements of a second sub-set of the transducer elements for a second of the at least two transmits. The method further includes extracting second harmonics from the echoes of the at least two transmits. The method further includes beamforming the extracted second harmonics. The method further includes generating an image based on the beamformed extracted second harmonics.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following describes an ultrasound imaging approach for deep penetration tissue harmonic imaging, with an array transducer and a focus or focal distance in a range from ten (10) to twenty (20) centimeters with a f-number of 5 or less, in which transducer elements are actuated pair-wise on transmit (two elements at a time) and individually on receive, and data either from two transmits using the same transmit aperture and two receives using two different receive apertures or from four transmits using two different transmit apertures and four receives using two different receive apertures. Such an approach is well-suited for in-line imaging in a lithotripter, where the region of interest (e.g., a kidney stone) is typically located twelve (12) to eighteen (18) cm from the transducer array. This approach is also well-suited for other applications with a region of interest in the range from ten (10) to twenty (20) centimeters.

Figure 1:
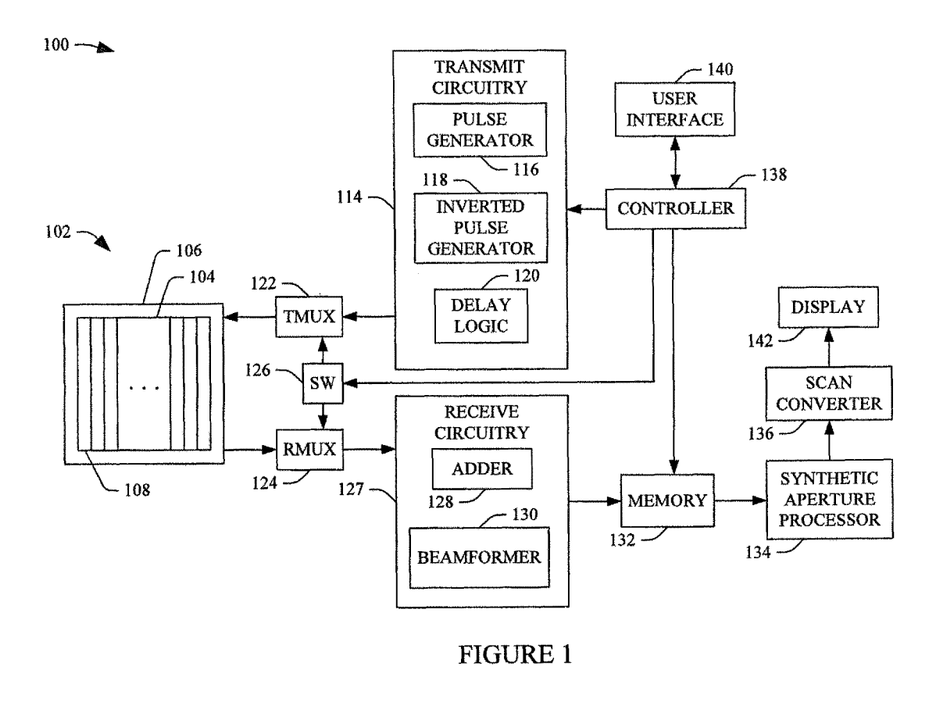
FIG. 1 illustrates an example ultrasound imaging system that includes componentry for harmonic imaging using pulse inversion.

Initially referring to FIG. 1, an example ultrasound imaging system 100 is illustrated. A transducer 102 includes a transducer array 104 and a housing 106 that houses the transducer array 104. The transducer array 104 includes a one dimensional (1D) phased, linear or curved array of N (e.g., N=32, 64, 128, 192, etc.) transducer elements 108 configured to sequentially, two or more at a time, transmit ultrasonic signals, which traverse an image of the field of view and an object therein, and receive echoes generated in response thereto. An echo, as referred to herein, is a result of an interaction between the transmitted ultrasonic signal and the object and includes a fundamental component, corresponding to the transmit frequency, and one or more harmonic components (e.g., second, third, fourth, etc.).

Figure 2:
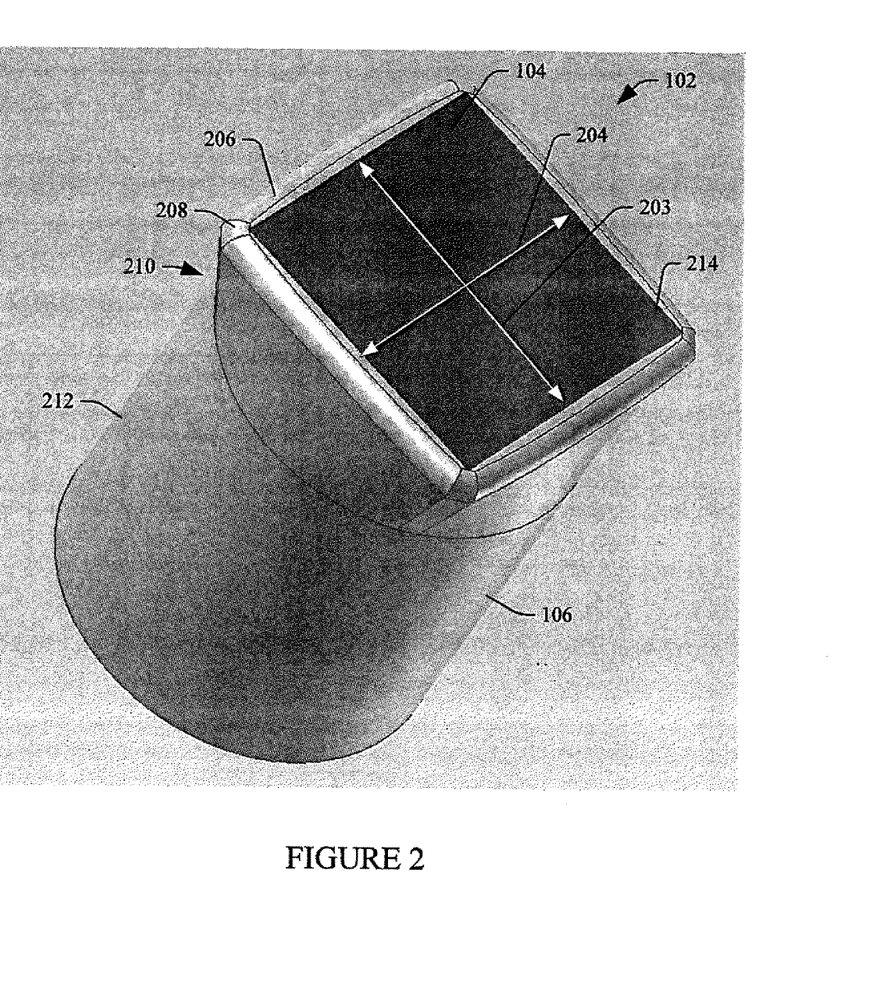
FIG. 2 illustrates an example transducer of the ultrasound imaging system of FIG. 1.

Briefly turning to FIG. 2, a non-limiting example of the transducer 102 is illustrated. The transducer array 104 has an approximately square footprint with an active length 203 (the pitch times the number of elements) and an active width 204 that are approximately equal. Suitable dimensions include, but are not limited to: 20×20 mm, 32×32 mm, and 50×50 mm. A rectangular and/or otherwise-shaped footprint is also contemplated herein. In this example, an optical window 214 of the housing 106 protects and shields the transducer array 104 from the environment. Inside the housing 106, the transducer array 104 is immersed in a liquid such as water, a gel, or the like (not visible in FIGS. 1 and 2). The housing 106 is hermetically sealed, which facilities ingress of liquid that could adversely affect imaging.

A front part 206 of the housing 106 includes a polymer. A suitable polymer is TPX (a product of Mitsui Petrochemical Industries, Ltd, a company of Tokyo, JP) overmolded with Elastosil (a product of Wacker Chemie AG, a company of Munch Germany). The overmolding renders the TPX and thus the front part 206 essentially shock wave resistant and provides damping of reflections. The illustrated housing 106 makes a gradual transition 208 from a generally square portion 210 of the front part 206 to a circular portion 212 of a tubular portion of the transducer 102. In one instance, this allows the transducer 102 to be rotated in its position and/or actuated along its axis. The housing 106 is electrically shielded, for example, with a metallization such as copper foil or other metallization.

Returning to FIG. 1, the focus of the transducer array 104 is in a range from ten (10) to twenty (20) cm, such as, for example, on the order of twelve (12), fifteen (15), seventeen (17), etc. cm. A focus in this range not only facilitates placing the focus in the region of interest for applications such as lithotripter, where the region of interest (e.g., a kidney stone) is typically located twelve (12) to eighteen (18) cm from the transducer array, but also delays the formation of harmonic components until after disturbing initial layers such as fatty layers at the skin and, in the case of lithotripsy, the possible water filled area that causes reverberations. However, such a focus may make the near field unusable, but for applications such as lithotripter, the near field can be sacrificed.

Focusing can be based on a traditional quadratic focus and/or other focus. Focusing can be achieved with internal focusing, a plano-concave lens and/or otherwise. Internal focusing and plano-concave lens approaches may facilitate mitigating negative apodization. For internal focusing, edges of an optical window are lifted (e.g., between 0.5 and 1.5 mm). With a plano-concave lens, such as a TPX lens, the edges of the lens are 3.5 mm thicker, for example, for a lens with a radius of curvature of approximately mm. The F number is less than five (5), for example, 4.8, 4.4, 3.8, etc., and the center frequency is less than four (4), for example, 3.5 MHz, 3 MHz, 2.8 MHz etc.

Transmit circuitry 114 includes a pulse generator 116, an inverted pulse generator 118, and delay logic 120. The pulse generator 116 generates actuation or excitation pulses, and the inverted pulse generator 116 generates inverted actuation or excitation pulses, which are inverted copies of the excitation pulses. The delay logic 120 delays transmission of an inverted excitation pulse based on a predetermined time delay from transmission of a corresponding actuation pulse. In a variation, the inverted pulse generator 118 is omitted, and a pulse inverter(s) inverts the ultrasound excitation pulse to generate the inverted excitation pulse.

A transmit multiplexer (TMUX) 122 routes the excitation pulses and the inverted excitation pulses to the transducer elements 108. In one instance, the transmit multiplexer 122 is configured to route an excitation pulse (or an inverted excitation pulse) in a pair-wise manner in which the excitation pulse (or the inverted excitation pulse) is routed sequentially to neighboring pairs of transducer elements 105 (e.g., to transducer elements 0 and 1, then to transducer elements 2 and 3, and so on) based on a predetermined time delay between excitations. In one mode of operation, this includes exciting the pairs, sequentially, with a first excitation pulse, a first inverted excitation pulse, a second excitation pulse, and a second inverted excitation pulse, for a total of four excitation pulses, to obtain data to construct each scan line. In other embodiments, an actuation pulse and/or an inverted excitation pulse can be routed to individual transducer elements and/or groups of more than two transducer elements.

A receive multiplexer (RMUX) 124 receives and routes echoes from the transducer array 104. In one instance, this includes receiving and routing echoes from individual transducer elements 108 of different sub-sets of the transducer elements 108. For example, in one instance, for the first excitation pulse and the first inverted excitation pulse of a pair of excitation pulses for a scan line, this includes individually receiving and subsequently routing echoes from even (or odd) numbered transducer elements such as transducer elements 0, 2, 4, . . . (or from transducer elements 1, 3, 5, . . . ). For the second excitation pulse and the second inverted second excitation pulse of the pair of excitation pulses, this includes individually receiving and subsequently routing echoes from odd (or even) numbered transducer elements such as transducer elements 1, 3, 5, . . . (or from transducer elements 0, 2, 4, . . . ).

A switch (SW) 126 switches between the transmit multiplexer 122 and the receive multiplexer 124 based on whether the transducer 102 is transmitting ultrasonic signals or receiving echoes.

Receive circuitry 127 includes an adder 128 that adds the echoes corresponding to the first excitation pulse and the first inverted excitation pulse producing a first combined signal and the echoes corresponding to the second excitation pulse and the second inverted excitation pulse producing a second combined signal. When adding echoes as such, the inverted copies of the fundamental components and the odd harmonic components cancel each other (i.e., adding to approximately zero) and the even harmonic components combine to double. As a result, the first and second combined signals include, for example, second harmonic components with a frequency (2f) that is twice the frequency (f) of the fundamental component.

A beamformer 130 applies time delays to the individual values of the first combined signal and sums, as a function of time, the time delayed values producing a first intermediate data or scan lines, and applies time delays to the individual values of the second combined signals and sums, as a function of time, the time delayed values producing a second intermediate data or scan lines. In this example, memory 132 stores the first intermediate data and the second intermediate data, which respectively correspond to the echoes received by the even (or odd) numbered transducer elements and the echoes received by the odd (or even) numbered transducer elements.

A synthetic aperture processor 134 generates a scan line based on the first and second intermediate data. In one instance, this includes adding the first and second intermediate data such that the generated scan line includes data for both even numbered and odd numbered transducer elements. A scan converter 136 scan converts the scan lines and generates an image to display, for example, by converting the scan lines to the coordinate system of the display. Generally, each image may be generated from fifty to five hundred scan lines, or more or less scan lines. The scan converter 136 can be configured to employ analog and/or digital scan converting techniques to convert the scan lines to an image for display via a display. Generally, a synthetic aperture is used to compensate for lack of channels. In configurations in which there are enough channels, the synthetic aperture processor 134 can be omitted. In an alternative embodiment, the adder 128 can be part of the synthetic aperture processor 134 and applied after beam forming.

A controller 138 controls various components of the system 100. For example, the controller 138 can control one or more of the switch 126, the transmit circuitry 114, the receive circuitry 127, and/or other component(s). A user interface 140, which is in electrical communication with the controller 138, includes one or more input devices (e.g., a button, a touch pad, etc.) and one or more output devices (e.g., a display screen, a speaker, etc.). Where the system 100 is configured for a plurality of different scanning modes (e.g., harmonic imaging, B-mode, etc.), the user interface 140 includes an input device which allows a user of the system 100 to indicate a desired scanning mode. A display 142 is used to visually present the generated image. In one instance, the image is presented in an interactive graphical user interface (GUI), which allows the user to selectively rotate, scale, and/or otherwise manipulate the displayed image. Such interaction can be through a mouse, keyboard, touch screen, or the like.

Figure 3:
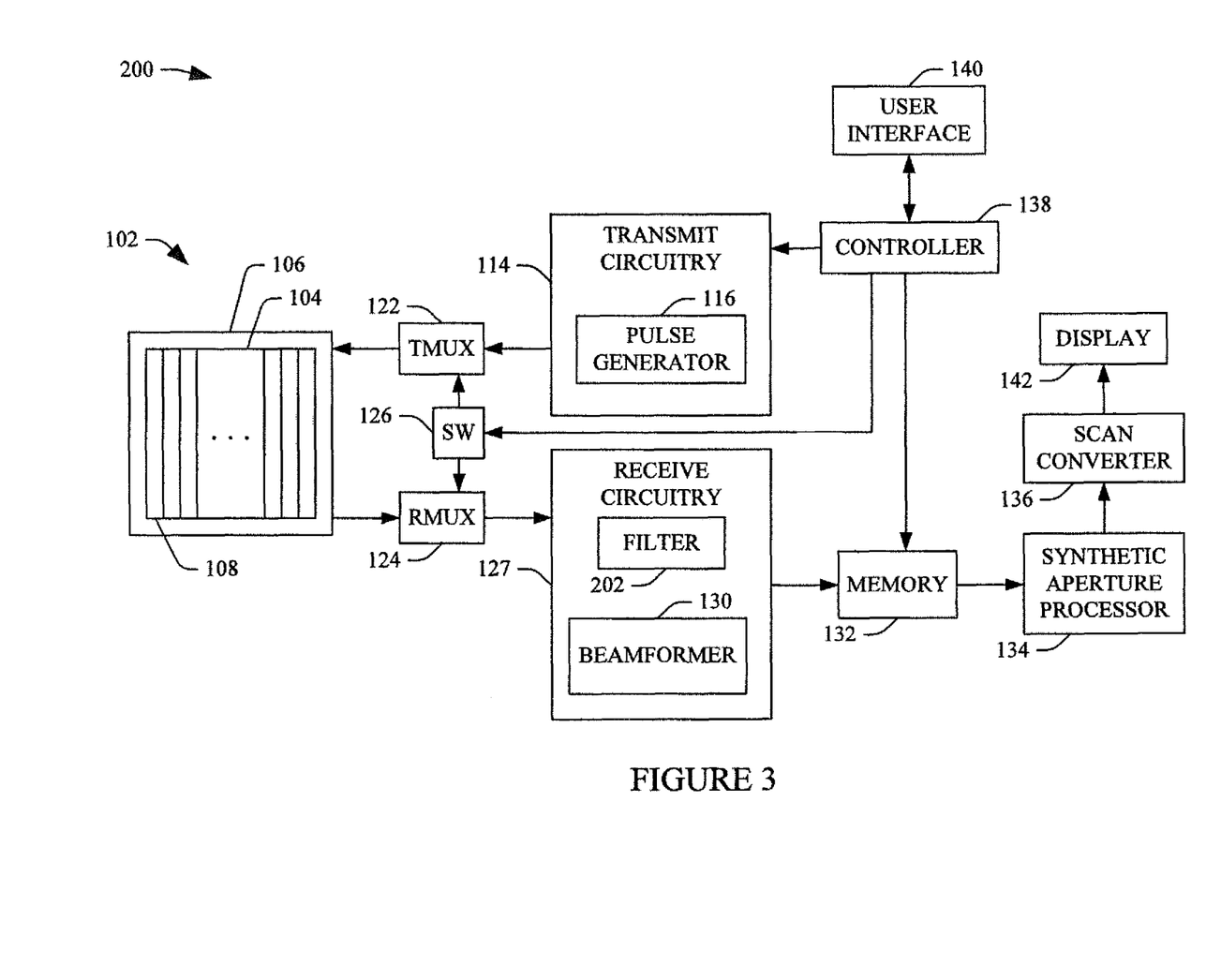
FIG. 3 illustrates an example ultrasound imaging system that includes componentry for harmonic imaging using filtering.

FIG. 3 illustrates a system 200 which is a variation of the system 100 of FIG. 1 in which the inverted pulse generator 118, the delay logic 120, and the adder 128 are omitted, and a filter 202 is included in the receive circuitry 127. In this embodiment, the filter 202 extracts the desired harmonic component from the received echoes. Since the frequency (2f) of the second harmonic component will be on the order of twice the frequency (f) of the fundamental component, a bandpass filter centered at the frequency (2f) can be used to pass the second harmonic component and filter the fundamental component. In a variation, the filter 202 can be part of the synthetic aperture processor 134 and applied after beam forming.

The second harmonic component can then be processed as discussed in connection with FIG. 1.

Figure 4:
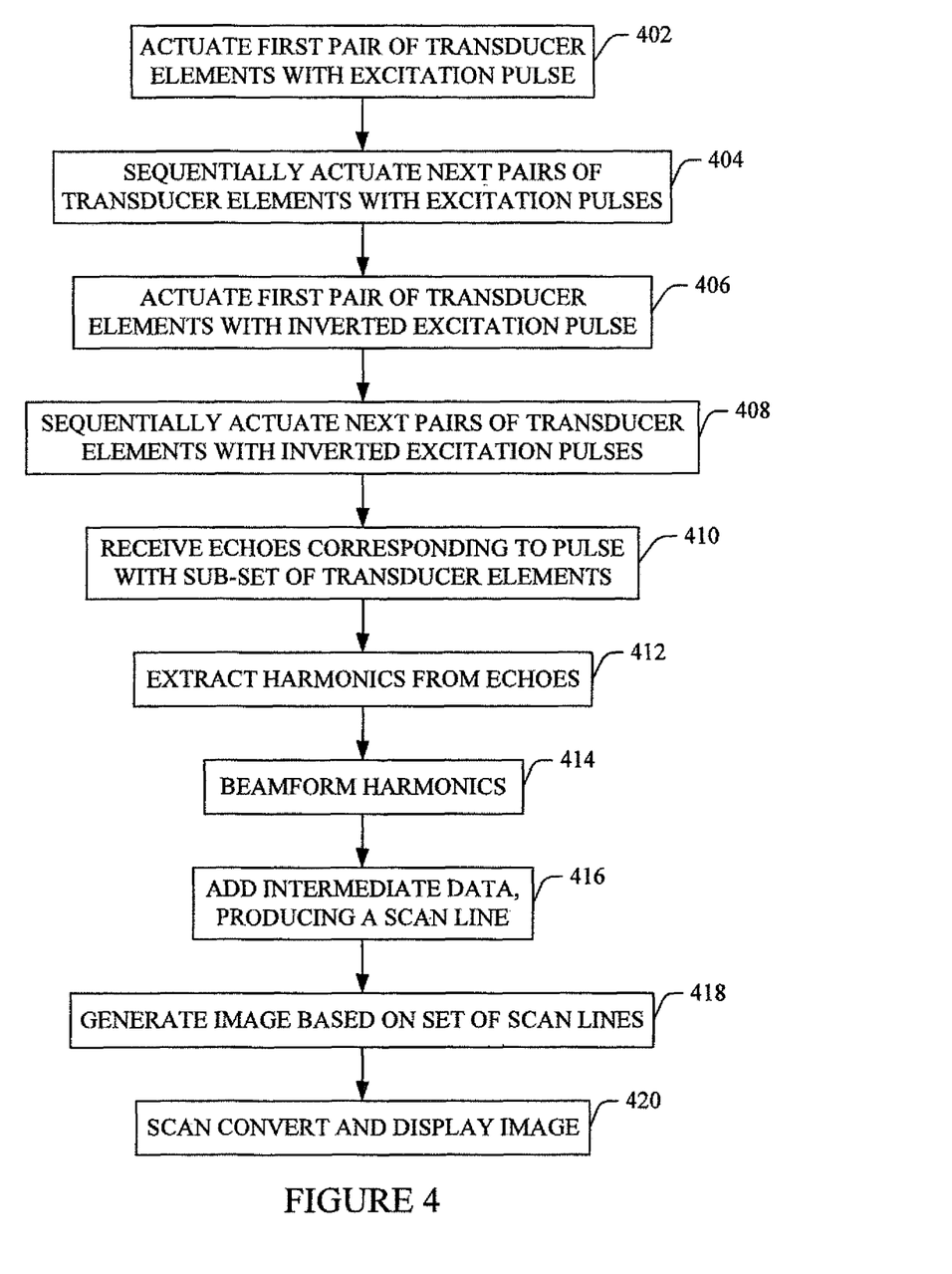
FIG. 4 illustrates an example method.

FIG. 4 illustrates an example method.

It is to be understood that the acts are provided for explanatory purposes and are not limiting. As such, one or more of the acts may be omitted, one or more acts may be added, one or more acts may occur in a different order (including simultaneously with another act), etc.

At 402, a first excitation pulse of a first set of pulses is concurrently conveyed to a first pair of neighboring transducer elements of a transducer array, actuating the pair of transducer elements to emit an ultrasonic signal.

At 404, after a predetermined time delay, a next excitation pulse of the first set of pulses is concurrently conveyed to a next pair of and neighboring transducer elements, actuating the next pair of transducer elements to emit an ultrasonic signal. This act is repeated for each pair of elements of the transducer array used to image an object.

At 406, a first inverted excitation pulse of the first set of pulses is concurrently conveyed to the first pair of neighboring transducer elements, actuating the pair of transducer elements to emit an ultrasonic signal.

At 408, after a predetermined time delay, a next inverted excitation pulse of the first set of pulses is concurrently conveyed to the next pair of and neighboring transducer elements, actuating the next pair of transducer elements to emit an ultrasonic signal. This act is repeated for each pair of elements of the transducer array used to image an object.

Acts 402 to 408 are repeated for a second set of pulses such that there are a total of four excitations for each transducer element.

At 410, echoes corresponding to the excitation pulses and to the inverted excitation pulses are received by a first subset of the transducer elements (e.g., even numbered or odd numbered transducer elements).

At 412, for each transducer element of the subset, the echoes for the excitation pulses and to the inverted excitation pulses are added together, extracting at least the second harmonic component from the echoes and cancelling the fundamental component.

At 414, the second harmonic components are delayed and summed, producing an intermediate data, which is stored in memory.

Acts 410 to 414 are repeated for a second subset of transducer elements (e.g., odd numbered or even numbered transducer elements).

At 416, the intermediate data is added, forming scan line based on both the even numbered and the odd numbered transducer elements.

Acts 402 to 416 are repeated, producing a plurality of different scan lines.

At 418, an image is generated based on the plurality of different scan lines.

At 420, the image is converted and displayed via a monitor.

Generally, the transmit and receive sequence of FIG. 4 can be summarized as shown below in Table 1. Transmitting on all elements creates a higher sound pressure and thereby also significantly higher non-linear components. The element pairs can be excited by a same transmitter, which can save cost, and is appropriate since the transmit frequency is half of the first harmonic that is the frequency of interest during receive.

TABLE 1

Pulse inversion sequence.

| | Transmit | | Receive | |
|---|---|---|---|---|
| Step | Element | Excitation | Element | Operation |
| 1 | All | Normal | Odd | Load to accumulator |
| 2 | All | Inverted | Odd | Add to accumulator |
| 3 | All | Normal | Even | Add to accumulator |
| 4 | All | Inverted | Even | Add to accumulator |

Figure 5:
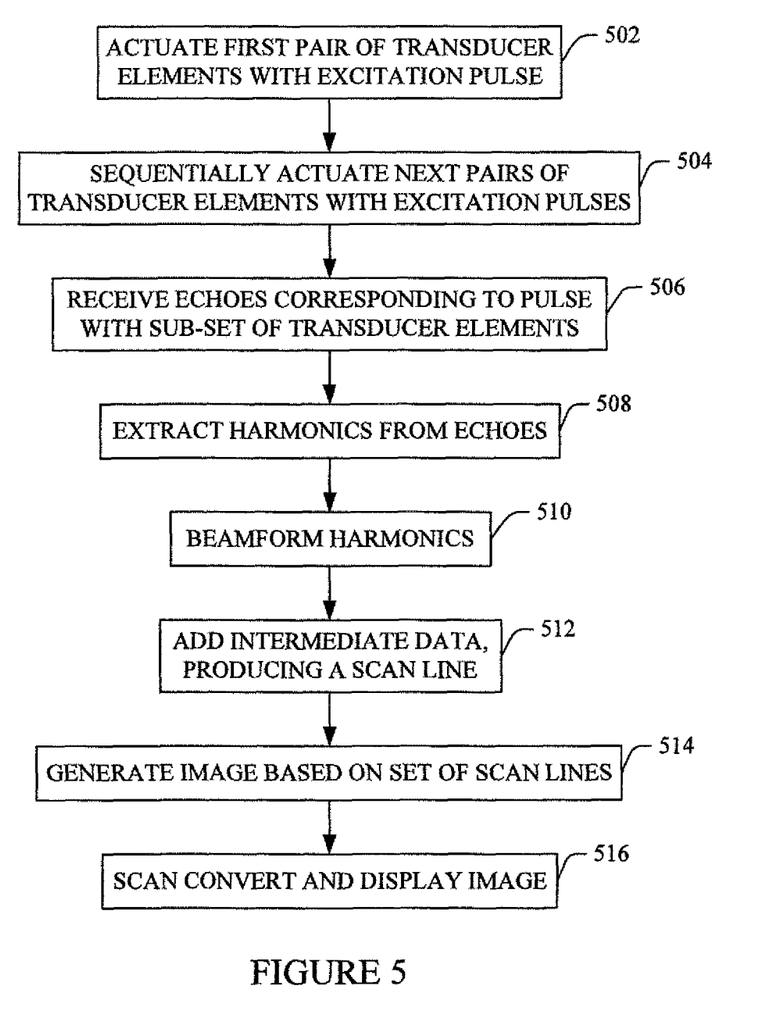
FIG. 5 illustrates another example method.

FIG. 5 illustrates an example method.

It is to be understood that the acts are provided for explanatory purposes and are not limiting. As such, one or more of the acts may be omitted, one or more acts may be added, one or more acts may occur in a different order (including simultaneously with another act), etc.

At 502, a first excitation pulse of a first set of pulses is concurrently conveyed to a first pair of neighboring transducer elements of a transducer array, actuating the pair of transducer elements to emit an ultrasonic signal.

At 504, after a predetermined time delay, a next excitation pulse of the first set of pulses is concurrently conveyed to a next pair of and neighboring transducer elements, actuating the next pair of transducer elements to emit an ultrasonic signal. This act is repeated for each pair of elements of the transducer array used to image an object.

Acts 502 to 504 are repeated for a second set of pulses such that there are a total of two excitations for each transducer element.

At 506, echoes corresponding to the excitation pulses are received by a first subset of the transducer elements (e.g., even numbered or odd numbered transducer elements).

At 508, the echoes are filtered, extracting the second harmonics.

At 510, the second harmonic components are delayed and summed, producing an intermediate data, which is stored in memory.

Acts 506 to 510 are repeated for a second subset of transducer elements (e.g., odd numbered or even numbered transducer elements).

At 512, the intermediate data are added, forming scan line based on both the even numbered and the odd numbered transducer elements.

Acts 502 to 512 are repeated, producing a plurality of different scan lines.

At 514, an image is generated based on the plurality of different scan lines.

At 516, the image is converted and displayed via a monitor.

Generally, the transmit and receive sequence of FIG. 5 can be summarized as shown below in Table 2. Again, transmitting on all elements creates a higher sound pressure and thereby also significantly higher non-linear components, and pairs can be excited by a same transmitter.

TABLE 2

Filtered sequence.

| | Transmit | | Receive | |
|---|---|---|---|---|
| Step | Element | Excitation | Element | operation |
| 1 | All | Normal | Odd | Load to accumulator |
| 2 | All | Normal | Even | Add to accumulator |

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer, including: an array of a plurality of transducer elements, wherein the transducer has a focus in a range of ten to twenty centimeters with a f-number of five or less;
   transmit circuitry that generates a first set of first excitation pulses that excites the plurality of transducer elements to emit first ultrasonic signals and, after a predetermined time delay, a second set of second excitation pulses that excites the plurality of transducer elements to emit second ultrasonic signals, wherein the transmit circuitry sequentially excites groups of two or more transducer elements with the first set of first excitation pulses and with the second set of second excitation pulses, exciting all of the transducer elements in each excitation, wherein the first set of first excitation pulses includes first pulses followed by first inverted copies of the first pulses;
   receive circuitry that receives first echoes generated in response to the first set of first excitation pulses and received by a first sub-set of the transducer elements, wherein the first echoes include echoes corresponding to the first pulses and first echoes corresponding to the first inverted copies of the first pulses and extracts a first set of harmonic components from the first echoes, and that receives second echoes generated in response to the second set of second excitation pulses and received by a second different sub-set of the transducer elements and extracts a second set of harmonic components from the second echoes, wherein the receive circuitry extracts the first set of harmonic components by adding the first echoes corresponding to the first pulses and the first echoes corresponding to the first inverted copies of the first pulses, which cancels fundamental components and odd harmonics of the first echoes and extracts second harmonic components of the first echoes, generating the first set of harmonic components; and a beamformer that beamforms the extracted first set of harmonic components producing first intermediate data and beamforms the extracted second set of harmonic components producing second intermediate data.

2. The system of claim 1, wherein the second set of second excitation pulses includes second pulses followed by second inverted copies of the second pulses and the second echoes include second echoes corresponding to the second pulses and second echoes corresponding to the second inverted copies of the second pulses, and the adder adds the second echoes corresponding to the second pulses and the second echoes corresponding to the second inverted copies of the second pulses, cancelling fundamental components and odd harmonics of the second echoes and extracting second harmonic components of the second echoes, generating the second set of harmonic components.

3. The system of claim 1, wherein the beamformer beamforms the first set of harmonic components generating the first intermediate data and that beamforms the second set of harmonic components generating the second intermediate data.

4. The system of claim 1, further comprising:
a scan converter that scan converts a plurality of scan lines, generating an image of an object.

5. The system of claim 1, wherein the first sub-set of the transducer elements corresponds to even or odd numbered transducer elements and the second sub-set of the transducer elements corresponds to the other of the even or odd numbered transducer elements.

6. The system of claim 1, wherein the ultrasonic signals have a center frequency on an order of three megahertz.

7. The system of claim 1, wherein the focus is on an order of twelve centimeters.

8. The system of claim 1, wherein the focus is on an order of fifteen centimeters.

9. The system of claim 1, wherein the transducer array has an approximately square footprint.

10. The system of claim 1, wherein the transducer array has an active length on an order of thirty-two millimeters and an active width on an order of thirty-two millimeters.

11. A method, comprising:
transmitting a first set of first excitation pulses that excites a plurality of transducer elements of an array to emit first ultrasonic signals and, after a predetermined time delay, a second set of second excitation pulses that excites the plurality of transducer elements to emit second ultrasonic signals, wherein groups of two or more transducer elements are sequentially excited with the first set of first excitation pulses and with the second set of second excitation pulses, wherein transmitting the first set of first excitation pulses comprises transmitting first pulses followed by first inverted copies of the first pulses;

receiving first echoes generated in response to the first set of first excitation pulses and received by a first sub-set of the transducer elements and extracting a first set of harmonic components from the first echoes, wherein receiving the first echoes includes receiving echoes corresponding to the first pulses and first echoes corresponding to the first inverted copies of the first pulses, and wherein extracting includes adding the first echoes corresponding to the first pulses and the first echoes corresponding to the first inverted copies of the first pulses, thereby cancelling fundamental components and odd harmonics of the first echoes and extracting second harmonic components of the first echoes, generating the first set of harmonic components, and receiving second echoes generated in response to the second set of second excitation pulses and received by a second different sub-set of the transducer elements and extracting a second set of harmonic components from the second echoes; and beamforming the extracted first set of harmonic components producing first intermediate data and beamforming the extracted second set of harmonic components producing second intermediate data, wherein the transducer has a focus in a range of ten to twenty centimeters and a f-number of five or less.

12. The method of claim 11, wherein transmitting the second set of second excitation pulses comprises transmitting second pulses followed by second inverted copies of the second pulses, and receiving the second echoes includes receiving echoes corresponding to the second pulses and second echoes corresponding to the second inverted copies of the second pulses; and further comprising: adding the second echoes corresponding to the second pulses and the second echoes corresponding to the second inverted copies of the second pulses, thereby cancelling fundamental components and odd harmonics of the second echoes and extracting second harmonic components of the second echoes, generating the second set of harmonic components.

13. The method of claim 11, further comprising:
beamforming the first set of harmonic components to generate the first intermediate data and beamforming the second set of harmonic components to generate the second intermediate data.

14. The method of claim 11, the beamforming, comprising: adding the first intermediate data and the second intermediate data, producing the scan line.

15. The method of claim 11, wherein the first sub-set of the transducer elements corresponds to even or odd numbered transducer elements and the second sub-set of the transducer elements corresponds to the other of the odd or even numbered transducer elements.

16. The method of claim 11, wherein the first set of first excitation pulses and the second set of second excitation pulses generate ultrasonic signals with a center frequency on an order of three megahertz.

17. An apparatus, comprising:
transmit circuitry that generates a first set of first excitation pulses that excites a plurality of transducer elements of a transducer to emit first ultrasonic signals, wherein the first set of first excitation pulses includes first pulses followed by first inverted copies of the first pulses;

receive circuitry that receives first echoes generated in response to the first set of first excitation pulses and received by a first sub-set of the transducer elements, wherein the first echoes include echoes corresponding to the first pulses and first echoes corresponding to the first inverted copies of the first pulses, and the first echoes are generated in response to a first interaction between the first ultrasonic signals and structure, and receives second echoes generated in response to the second set of second excitation pulses and received by a second sub-set of the transducer elements, wherein the second echoes include echoes corresponding to the second pulses and second echoes corresponding to the second inverted copies of the second pulses, and the second echoes are generated in response to a second interaction between the second ultrasonic signals and structure;

an adder that adds the first echoes corresponding to the first pulses and the first echoes corresponding to the first inverted copies of the first pulses, cancelling fundamental components and odd harmonics of the first echoes and extracting second harmonic components of the first echoes, extracting a first set of harmonic components, and that adds the second echoes corresponding to the second pulses and the second echoes corresponding to the second inverted copies of the second pulses, cancelling fundamental components and odd harmonics of the second echoes and extracting second harmonic components of the second echoes, extracting a second set of harmonic components; and a beamformer that beamforms the extracted first set of harmonic components producing first intermediate data and beamforms the extracted second set of harmonic components producing second intermediate data.

18. The apparatus of claim 17, wherein the transducer has a focus in a range of ten to twenty centimeters.

19. The apparatus of claim 17, wherein the transducer has a f-number of five or less.

* * * * *